United States Patent [19]

Figuera

[11] 4,425,670
[45] Jan. 17, 1984

[54] CARDIAC VALVULAR PROSTHESIS WITH RHEODYNAMIC DISC

[75] Inventor: Diego Figuera, Madrid, Spain

[73] Assignee: Datascope Corporation, Oakland, N.J.

[21] Appl. No.: 283,562

[22] Filed: Jul. 15, 1981

[30] Foreign Application Priority Data

Jun. 4, 1981 [ES] Spain ............................... 502787

[51] Int. Cl.³ .............................................. A61F 1/22
[52] U.S. Cl. ........................................ 3/1.5; 137/527; 137/527.8
[58] Field of Search .................. 3/1.5; 137/527, 527.8

[56] References Cited

U.S. PATENT DOCUMENTS

| | | | |
|---|---|---|---|
| 3,508,281 | 4/1970 | Cromie | 3/1.5 |
| 3,546,711 | 12/1970 | Bokros | 3/1.5 |
| 3,825,956 | 7/1974 | Child | 3/1.5 |
| 3,926,215 | 12/1975 | Macleod | 3/1.5 X |
| 4,159,543 | 7/1979 | Carpentier | 3/1.5 |

Primary Examiner—Ronald L. Frinks
Attorney, Agent, or Firm—Fitzpatrick, Cella, Harper & Scinto

[57] ABSTRACT

A cardiac valvular prosthesis comprising an occluder disc, a supporting ring pivotally supporting said disc, and a suturing ring arranged on an outer portion of said supporting ring and adapted to facilitate suturing to the annulus of a cardiac valve to be replaced, said occluder disc having a hydrodynamic shape, an eccentrically positioned rotational axis far from the obturation plane of the disc, and hinges located in the central area of said disc, said occluder disc being pivotable between an open position disposed at an angle which is 90° with respect to the supporting ring and a closed position wherein said disc is disposed at an angle of approximately 15° with respect to said supporting ring.

16 Claims, 17 Drawing Figures

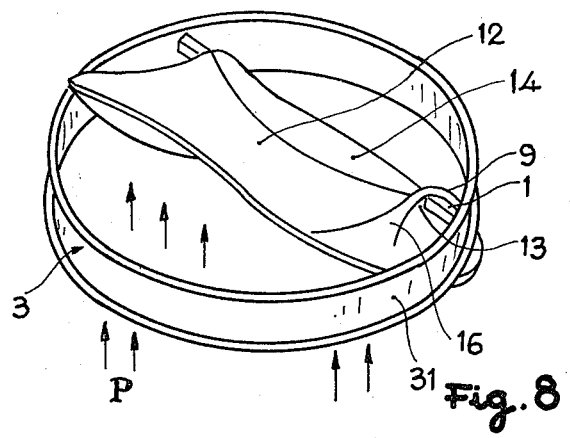
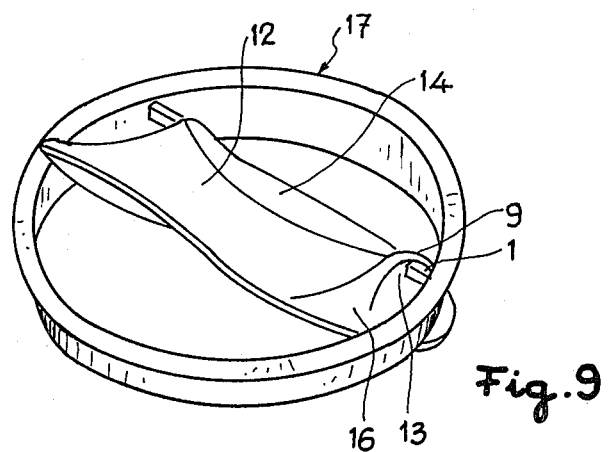
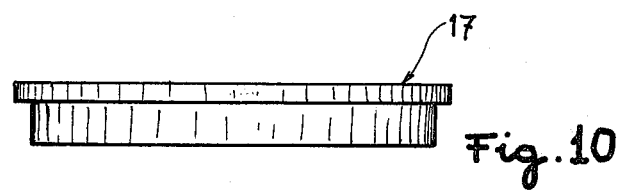

CARDIAC VALVULAR PROSTHESIS WITH RHEODYNAMIC DISC

BACKGROUND OF THE INVENTION

This invention relates to a cardiac valvular prosthesis which is used as a substitute for diseased cardiac valves. The cardiac valvular prosthesis of this invention can also be used in an artificial heart, presently in experimentation, and also in "valvular conduits" that can be used in the correction of congenital cardiac diseases.

At present, there are many cardiac prostheses in existence, Many of them are in industrial production, and others are in the experimental phase. Nevertheless, until now, all of the prostheses that have been used have presented various inconveniences of different degrees, of which the most important are the following:

1. Insufficient disc opening. This occurs with a prior art valve known as the Bjork-Shiley's valve, whose design prevents an opening of more than 60°. This causes the appearance of high pressure gradients throughout the valve which is especially severe in small sizes, causing the heart to overwork itself, thus preventing the use of this valve in extreme cases. This also creates an unfavorable hydrodynamic situation in the minor segment of the valve hole which, because of its small size, only permits a reduced flow through it, which is far slower than that of the major segment, thus producing blood stagnation. This is not the case with the cardiac valvular prosthesis of the present invention, since the inventive valve has a complete opening and there are no significative differences in the blood stream between the two disc segments and the gradients are minimal. Therefore, the overworking of the heart with the valve of the present invention is almost nil.

2. Production of turbulence. The majority of the mechanical valves in existence, at present (Bjork-Shiley, and others such as Omniscience, St. Jude, Starr-Edwards, et.), produce severe turbulence caused, in part, by deficient disc opening, which never reaches 90° in any of the models, because of their form and joining systems. The complete opening and the hydrodynamic design of the disc or occluder in the valve of the present invention avoids this problem.

3. Tendency to thrombosis. All mechanical valves tend to produce thrombosis. The prosthesis of the present invention attempts to reduce this problem to a minimum. A production factor of thrombosis is turbulence. The type of hinges of the occluder with the supporting ring and the location site of these hinges are also important. In general, many of the present valves (St. Jude, Omniscience, Kaster-Lillehey) have their hinges in the disc's periphery, making contact with the inside of the supporting ring. This is a serious inconvenience, as this zone has zero flow, according to Newton's Law of Fluids, thus having a tendency to cause stagnation and thrombosis. One way of reducing thrombosis in the hinges of the disc with the ring, would be to situate these hinges in the central area of the disc where, according to the mentioned Newton's Law of Fluids, the current is of maximal intensity.

4. Non-hydrodynamic designs of the disc and unfavorable position when open. It is believed that the mechanical valves in existence, at present, have not sufficiently taken into consideration the hydrodynamic factors when designing the obturator discs, which is considered to be essential in the avoidance of turbulence and thrombosis. Also erroneous in the prior art valves is the oblique position of the disc when fully open.

5. Flat design of the ring in the aortic valves. All of the mechanical cardiac valves in use, present a flat implantation ring. This is adequate when they are used in mitral or tricuspid positions, because the cardiac annuluses of these valves are flat too; but it is very inconvenient when the valve is an aortic one, because the aortic annulus of the patient has a scalloped shape.

The valve of the present invention, solves this problem, with a scalloped implantation ring which can be fully adapted to the annulus of the patient. This not only reduces tension in the suture line, but it protects the coronary ostium and allows the implantation of a larger sized valve, reducing the transvalvular gradients.

6. Poorly-washed hinges. As it has been noted above, the hinge zone between the ring and the obturator is very prone to produce thrombos. Therefore, it is necessary to design this area in such a way so that the function of the valve guarantees the washing-out of the hinges. In the present invention the hinges are located in the rapid flow area. Furthermore, there are no profound holes or orifices that may produce stagnation of the blood, and the joint cavity is flat, superficial, large and totally open. An oblique surface precedes the hinge area, and this canalizes the blood flow towards the hinge during opening and closing, inversely to the advancing of the contact line of the hinge with the joining part of the disc. This condition guarantees a proper washing-out of the joining surface.

SUMMARY OF THE INVENTION

An object of this invention is to provide a new type of cardiac valvular prosthesis characterized by the fact that the occluder has a very complex rheodynamic design that has been the result of an exhaustive hydrodynamic study. The disc is called "rheodynamic" because the blood stream, by itself, can open the disc 90°, stabilize it in this position during the systole time, and close it back during the dyastole. This is possible because of the special shape of the disc and its hinges.

A further object of this invention is to provide a new type of cardiac valvular prosthesis having among its most important features the fact that the disc is a totally asymmetrical one with hinges on the closing side and with two joining protuberances and two unequal segments, both with concave, cylindrical surfaces and having a rotation axis which is separated far from the obturator plane.

A further object of the present invention is to provide a new type of cardiac valvular prosthesis having hinges located in the central area of the disc to avoid the peripheric blood stagnating area, and having a shape providing free flushing while the valve is in motion.

To attain the above-mentioned objects, this invention provides a cardiac valvular prosthesis which comprises an occluder disc, a supporting ring pivotally supporting said disc, and a suturing ring on the outer portion of said supporting ring for suturing to the annulus of a cardiac valve to be replaced, said occluder disc having a hydrodynamic shape and a rotation axis which is eccentrically placed so that it is situated far from the obturation plane, and hinges positioned in the central area of said disc, adapted so that the occluder disc opens to an angle of 90° with respect to said supporting ring, said disc being in a position which is an oblique angle with respect to said supporting ring when it is in its closed position.

The main advantages of the cardiac valvular prosthesis of this invention are the total opening of the disc i.e. to 90°; the fact that there is minimal turbulence because of laminar flow along the disc; minimal transvalvular gradient; minimal backflow; minimal hemolysis; and, a good possibility of very reduced thrombosis formation in the patient.

BRIEF DESCRIPTION OF THE DRAWING

This invention can be fully understood from the following detailed description with reference to the accompanying drawing in which:

FIG. 8 shows the occluder disc in the supporting ring during the opening of the valve;

FIG. 9 is a view of the occluder disc similar to that of FIG. 8, i.e. within the supporting ring during the opening and also showing the suturing ring;

FIG. 10 is a side view of the suturing ring;

DESCRIPTION OF PREFERRED EMBODIMENT

With reference to the drawings, the cardiac valvular prosthesis of the present invention can be seen in its total aspect in FIGS. 8 to 13 and consists of three wall-differentiated parts, namely a mobile part or occluder disc 20, a supporting ring 3, and a suturing ring 17.

Figure 4:
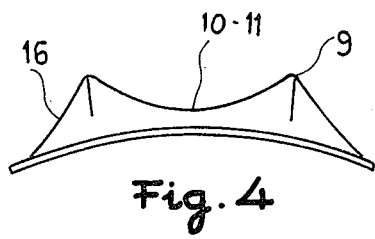
FIG. 4 shows a view of the occluder disc as seen from the edge of the major segment thereof.
Figure 5:
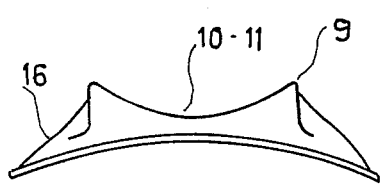
FIG. 5 is a view of the occluder disc as seen from the edge of the minor segment thereof.

The occluder disc 20 will now be described with reference to FIGS. 3, 4 and 5. The occluder disc may be circular or elliptical in shape and has two sides, namely a closing side or joining side, and an opening side or a non-joining side.

More particularly, with reference to FIG. 3 which shows the occluder disc 20 from its joining or closing side, there are two protuberances 9 and 9' having a maximum height which is in the portion which is joined with the pivots 1 and 1' which will be described below. Both protuberances 9, 9', determine a chord 10, 11 which comprises the rotational axis and which divides the surface of the disc into two unequal segments, hereinafter called a major segment 7 of the disc and minor segment 8 of the disc.

Figure 6:
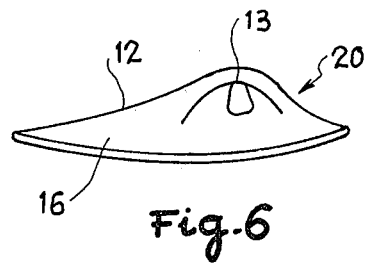
FIG. 6 is a side view of the occluder disc, and without the supporting ring.
Figure 6A:
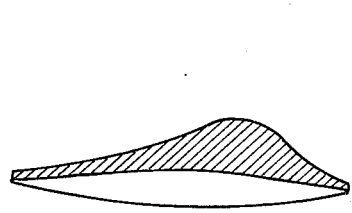
FIG. 6a shows a cross-section of the occluder disc along a plane perpendicular to the rotational plane.

The major segment 7 of the disc 20 lowers in height from the plane that contains the rotational axis to the periphery of the disc in such a manner that the portion of the major segment 7 which is between the two joining protuberances 9, 9' constitutes a concave cylindrical surface 12. This surface 12 is inclined in relation to the opening side of the disc as will be apparent from FIGS. 3, 4 and 5. At the same time, the concave cylindrical surface 12 is also slightly concave perpendicularly to the joining line of the protuberances 9, 9' as is evident in FIG. 6 of the drawing.

The protuberances 9, 9' have, in their lateral portions, cavities 13 shaped like a sector of a circle whose arc is less than a quarter of the circumference and arranged in such a manner that the vertex is positioned as far from the obturation plane of the disc 20 as possible.

Figure 3:
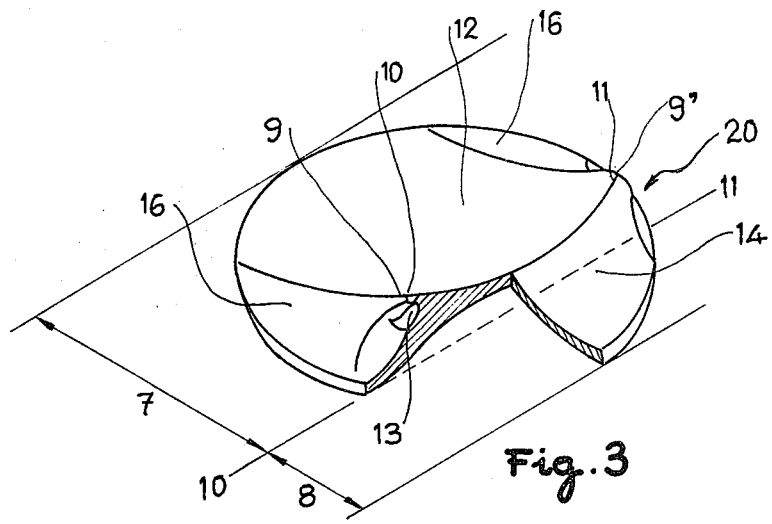
FIG. 3 shows the closing or joining side of the occluder disc of the cardiac valvular prosthesis of the present invention.

As will appear more particularly from FIG. 3 of the drawing, two inclined planes 16 are formed in the major segment 7 from the extreme edge of the concave cylindrical surface 12 up until the lateral edges of the disc 20. This shape is very important in order to facilitate the closing, as well as the washing-out of the joints, driving the blood flow below the pivots 1, 1' and through the hinge cavities 13, in every movement of the opening and closing of the valve.

The minor segment 8 of the occluder disc 20 also has a concave cylindrical surface 14 which is inclined and which has a thickness which diminishes as far as the edge of the disc 20. This is very important from the hydrodynamic point of view because it acts as a stabilizer in the fully opened position of the valve and helps the valve to reach the fully opened position.

The opening side or the non-joining side of the disc 20 is the one opposite to the closing side just described above. The opening side of the disc receives the blood flow during the opening of the valve. It has a curved shape resembling a saddle, concave in the direction of rotational axis and slightly convex or flat in the direction perpendicular to the latter. This will be evident upon inspection of FIGS. 3 to 6 of the drawing. The shapes of both sides of the disc 20 described above, result from a profound hydrodynamic study and are very important for the proper functioning of the valve.

Figure 1:
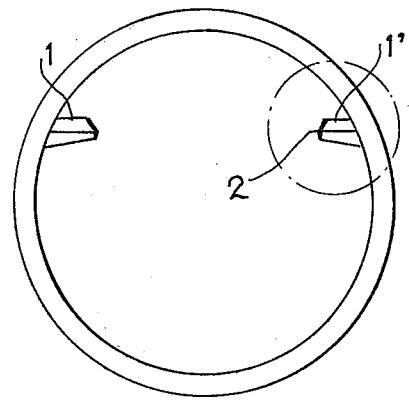
FIG. 1 is a plan view of the supporting ring used in the cardiac valvular prosthesis of the present invention.
Figure 2:
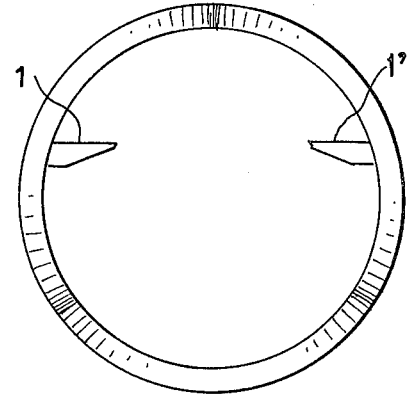
FIG. 2 is plan view of another embodiment of the supporting ring for aortic implantation of the valve.
Figure 2A:
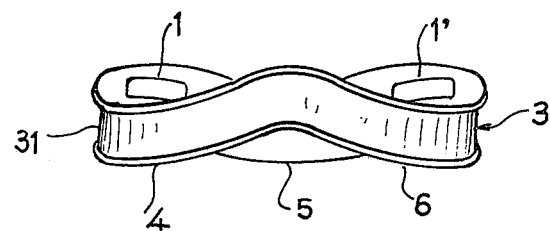
FIG. 2a is a side view of the supporting ring shown in FIG. 2.

Turning now to FIGS. 1 to 2a, the supporting ring 3 will now be described. As shown, the supporting ring is circular in shape and has a groove 31 in its outer portion where the suturing ring 17 is adapted to be positioned.

The supporting ring 3 can have a number of different shapes and the invention is not limited thereto. Thus, in FIG. 1 the supporting ring is shown as being flat. In FIG. 2 a further embodiment of the supporting ring is shown having three scallops 4, 5 and 6 which allow and make easier its adaptation to a patient's aortic annulus when the valve is implanted.

Figure 1A:
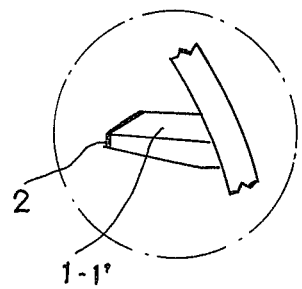
FIG. 1a is an enlarged detail of the supporting ring showing the pivot.
Figure 1B:
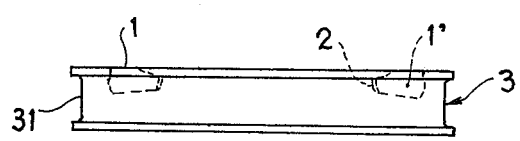
FIG. 1b is a side view of the supporting ring shown in FIG. 1.

In both embodiments of the supporting ring there are two pivots 1, 1' which are located opposite each other as shown in the FIGS. 1 and 2. These pivots serve as the points of rotation or joints with the occluder disc 20. The length of each pivot 1, 1' is made adequate such as to situate the resulting hinge in the central area of the valvular orifice, i.e. where the flow is greater. The joining part of the pivots is only the oblique line 2 of the inner extreme portion thereof, marked with a thick line in FIG. 1a of the drawing. The remainder of the pivot is not essential and merely gives strength to the hinge line. The oblique hinge line 2 of the pivot 1, 1' as shown in the detail of FIG. 1a is essential to limit the opening of the disc 20 and to prevent this from becoming greater than 90° with respect to the supporting ring 3 due to the fact that when reaching this total opening it makes contact with the edge of that sector of the circle of the joining cavities 13 which are on the outer sides of the protuberances 9, 9' of the disc 20 as will appear from FIGS. 3 and 6 of the drawing. Turning now to FIGS. 9 and 10 of the drawing, the suturing ring 17 is shown therein. This ring is made of soft, porous tissue of compatible bio-material. The suturing ring 17 adapts to the groove 31 in the outer part of the supporting ring 3. It is made so that it has the proper shape and size in order to facilitate suturing to the annuluses of the different cardiac valves to be replaced.

Figure 7:
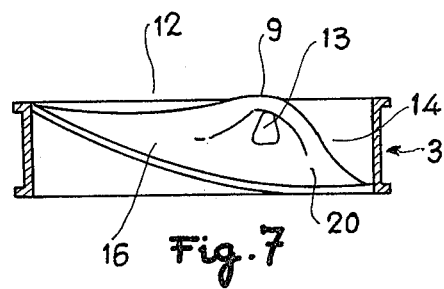
FIG. 7 is a side view of the occluder disc positioned within the supporting ring.
Figure 11:
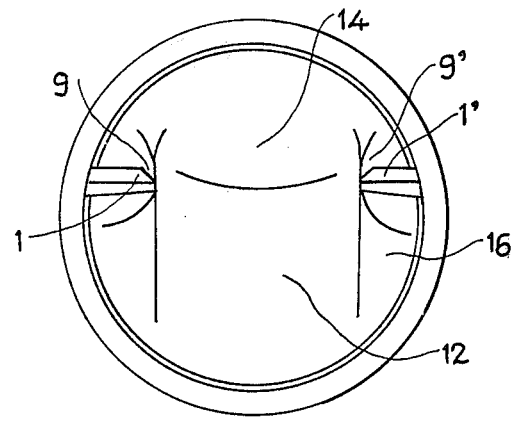
FIG. 11 is a plan view of the occluder disc and supporting ring as seen from the joining or closing side.

The operation of the valve will now be described. FIG. 7 of the drawing shows the valve at its starting point in the closed or rest position. It will be noted that the occluder disc 20 is in a position which is oblique with respect to the supporting ring 3 and forms an angle of approximately 15° therewith. This oblique, initial, position of the disc has the advantage of limiting the range of the disc until it reaches its total opening, i.e. at an angle of 90° with respect to the supporting ring 3. This is also favorable during the closing of the valve because regurgitation (back-flow) is reduced.

Figure 12:
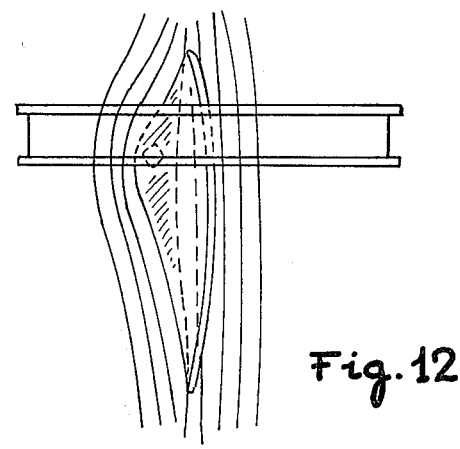
FIG. 12 shows a side view of the occluder disc and supporting ring with the valve fully opened i.e. in the 90° position; the laminar flow is represented by the lines along the occluder disc.
Figure 13:
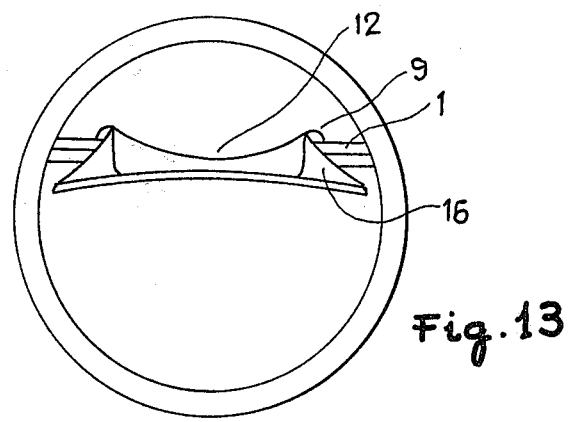
FIG. 13 shows the plan view of the cardiac valvular prosthesis of the present invention with the valve fully opened as seen from above (downstream).

The opening of the valve is shown in FIG. 8 of the drawing and is produced when pressure P is applied against the nonjoining side due to the fact that the rotational axis of the disc 20 is asymmetrical. Therefore the force received by the major segment 7 is far superior to that received by the minor one 8, and the point where this force is applied also produces still a greater imbalance of the rotational pair. As a result, a very low gradient of pressure between both sides is enough to open the valve totally. The profile is favorable to the blood flow when the disc is opened, because of the hydrodynamic design and the resistance to the blood flow is minimum. The shape of the disc also produces a laminar flow which is shown in FIG. 12 by the lines along the disc and therefore it avoids turbulence. The opening of the valve up to 90° with respect to the supporting ring 3 is limited by the oblique edge 2 of the pivots 1, 1' as described above. This is limited by the edge of the sector of the circle joining the cavities 13 of the disc 20. The disc 20 has therefore risen to its open position in relation to the ring, due to the eccentric situation of the rotational axis. The disc 20 is separated from the supporting ring 3 far enough so that the blood does not stop at any point of the periphery of the disc, thus avoiding thrombosis, which is one of the disadvantages of the prior art valves. The length and position of the pivots 1, 1' make the rotational points of the hinges far from the periphery of the disc and place them in the area of the rapid flow of blood, thereby reducing danger of thrombos formation.

After the valve has been opened or partially opened, and pressure is then received on the joining or closing side of the disc 20, the eccentricity and the far position of the rotational axis, combined with the inclined position of the cylindrical concave surface 12 of the major segment 7 and with the triangular lateral planes 16, produce the formation of a very strong rotational pair. This arrangement causes the valve to close very quickly and stop the blood flow. Because the closing position of the valve is achieved when the disc 20 is oblique with respect to the supporting ring 3 (approximately 15° as noted above), the path to achieve the closing of the valve is shorter and the regurgitation (back-flow) is reduced. In the closed position, the disc 20 overlaps the supporting ring 3 in the minor segment 8 and, optionally in part of the major segment 7, which achieves a compromise between regurgitation, hemolysis and washing of the hinges.

The invention is not limited to the embodiments described and represented hereinbefore and various modifications can be made thereto without exceeding the scope of the invention as claimed.

What I claim is:

1. A cardiac valvular prosthesis comprising an occluder disc, a supporting ring pivotally supporting said disc, and a suturing ring arranged on an outer portion of said supporting ring and adapted to facilitate suturing to the annulus of a cardiac valve to be replaced, said occluder disc having a hydrodynamic shape, an eccentrically positioned rotational axis far from the obturation plane of the disc, and hinges located in the central area of said disc, said occluder disc being formed with a closing side and an opening side, said closing side comprising two joining protuberances each having a cavity in its outer side of a shape which is slightly less than a quarter of a circle and arranged such that the vertex thereof is as far from the obturation plane as possible, said cavities defining an eccentrically positioned rotational axis, said closing side further comprising a chord determined by said protuberances and dividing said disc into unequal major and minor segments, said major segment progressively diminishing in thickness between said opening side and said closing side from a principal plane defined by said chord and containing said rotational axis to the periphery of said disc and having a concave surface with a substantial concavity in the direction of said principal plane and a less substantial concavity in the direction perpendicular to said principal plane, and two triangularly shaped inclined planes having one side curved and extending from said concave surface to the edge of said disc and continuing toward said principal plane and terminating in said cavities such that a flow of blood can be driven through said cavities, said minor segment also having a concave surface with a thickness between said closing side and said opening side which diminishes from said principal plane to the edge of said disc, and said opening side of said disc being opposite to said closing side and saddle-shaped, concave in the direction of said principal plane and slightly convex or flat in a direction perpendicular to said principal plane, said occluder disc further being pivotable between an open position disposed at an angle which is 90° with respect to the supporting ring and a closed position wherein said disc is disposed at an oblique angle with respect to said supporting ring.

2. A cardiac valvular prosthesis according to claim 1, wherein said supporting ring has a groove in said outer portion thereof for receiving said suturing ring, said suturing ring being made from a compatible, biomaterial facilitating implantation to the annulus of a patient, said supporting ring being provided on an inner portion thereof with two opposing pivots, each terminating in an oblique edge, said pivots joining with their edges in said cavities to form said hinges, each of said pivots terminating in a vertex, said vertices being the location of rotation of said occluder disc, at least one said oblique edge on each of said pivots limiting the opening of said disc by making contact with the limit of the sector of the circle of said cavity in which it is received, and the length and position of said pivots being arranged to ensure that said hinges are located in the central area of said disc.

3. A cardiac valvular prosthesis comprising:

a supporting ring;

an occluder disc having a hydrodynamic shape formed with a closing side including two generally axially projecting protuberances spaced radially inwardly from the periphery of said disc, each protuberance having a cavity in its outwardly facing side located in a central region of said disc, said cavities together defining an eccentrically positioned axis of rotation of said disc, said closing side further including a principal plane defined between said protuberances that includes said axis of rotation, the surface of said closing side defining an arc lying in said principal plane that smoothly and continuously connects the extremes of said protuberances with the thickness of said disc progressively diminishing from said arc to said periphery in the direction perpendicular to said principal plane; and two opposing pivots projecting from an inner portion of said ring, each being received in one said cavity at a location spaced from the periphery of said disc and said ring in the central region of said disc, said pivots and said cavities together comprising hinges for providing for pivoted movement of said disc relative to said ring about said axis of rotation, between open and closed positions, whereby laminar flow of blood over said closing side of said disc and washing of said pivots and said cavities occur when blood flows through said prosthesis with said disc in said open position.

4. A cardiac valvular prosthesis comprising:

a supporting ring; and an occluder disc supported for pivoted movement in said ring between open and closed positions and including:

an opening side, and a closing side formed with two joining protuberances spaced from the periphery of said disc, a chord extending continuously between said protuberances and defining a principal plane at an eccentric position that includes an axis of rotation of said disc relative to said ring, said principal plane dividing said disc into unequal major and minor segments, said major segment progressively diminishing in thickness between said opening side and said closing side from said principal plane to the periphery of said disc, said closing side in said major segment further having a concave surface with a substantial concavity in the direction of said principal plane and a less substantial concavity in the direction perpendicular to said principal plane, and two triangularly shaped inclined planes each having one side, curved and extending from said concave surface to the periphery of said disc and continuing toward said principal plane; said closing side in said minor segment also having a concave surface, said minor segment progressively diminishing in thickness between said opening side and said closing side from said principal plane to the periphery of said disc.

5. A cardiac valvular prosthesis according to claims 1, 2, 3 or 4, wherein said supporting ring has three scallops to facilitate adaptation to the aortic annulus of a patient.

6. A cardiac valvular prosthesis according to any one of claims 1, 2, 3, or 4 wherein said occluder disc is disposed at an angle of approximately 15° with respect to said supporting ring and overlaps part of said supporting ring when said disc is in said closed position.

7. A cardiac valvular prosthesis according to claims 3 or 4 further comprising a suturing ring made of a compatible, biomaterial facilitating implanation to the annulus of a patient, and wherein said supporting ring is formed with an annular groove in an outer surface thereof for receiving said suturing ring.

8. A cardiac valvular prosthesis according to claim 3 wherein said disc also comprises an opening side and wherein said principle plane divides said disc into unequal major and minor segments; said major segment progressively diminishing in thickness between said opening side and said closing side from said principal plane to the periphery of said disc, said closing side in said major segment having a concave surface with a substantial concavity in the direction of said principal plane and a less substantial concavity in the direction perpendicular to said principal plane, and two triangularly shaped inclined planes each having one side curved, extending from said concave surface to the periphery of said disc, and continuing toward said principal plane; said closing side in said minor segment also having a concave surface, said minor segment progressively diminishing in thickness between said opening side and said closing side from said principal plane to the periphery of said disc.

9. A caridac valvular prosthesis according to claim 4 wherein each said protuberance has a cavity in its outwardly facing side located in a central region of said disc, said cavities together defining said eccentrically positioned axis of rotation, said prosthesis further comprising two opposing pivots projecting from an inner portion of said ring, each being received in one said cavity at a location spaced from the periphery of said ring in the central region of said disc, said pivots and said cavities together comprising hinges for providing for pivoted movement of said disc relative to said ring about said axis of rotation between open and closed positions, whereby laminar flow of blood over said closing side of said disc and washing of said pivots and said cavities occur when blood flows through said prosthesis with said disc in said open position.

10. A cardiac valvular prosthesis according to claims 8 or 9 wherein each of said triangularly shaped planes terminates in one of said cavities whereby a flow of blood can be driven through said cavities.

11. A cardiac valvular prosthesis according to claims 3 or 9 wherein each said cavity is bounded by a surface having an arcuate cross section.

12. A cardiac valvular prosthesis according to claim 11 wherein said arcuate cross section constitutes less than one quarter of a circle.

13. A cardiac valvular prosthesis according to claim 11 wherein each of said pivots terminates in an oblique edge which limits the opening of said disc when it makes contact with an extreme of the arcuate surface of said cavity in which it is received.

14. A cardiac valvular prosthesis according to claims 3 or 9 wherein said hinges mount said disc for pivoted movement to said open position with said disc disposed at an angle of about 90° relative to said ring.

15. A cardiac valvular prosthesis according to claim 3 wherein said disc further comprises an opening side opposite said closing side, said opening side being saddle-shaped, having a surface which is concave in the direction of said principal plane and which is flat or convex in the direction perpendicular to said principal plane.

16. A cardiac valvular prosthesis according to claim 4 wherein said opening side of said disc is saddle-shaped having a surface which is concave in the direction of said principal plane and which is flat or convex in that direction perpendicular to said principal plane.

* * * * *

UNITED STATES PATENT AND TRADEMARK OFFICE
CERTIFICATE OF CORRECTION

PATENT NO. : 4,425,670

DATED : January 17, 1984

INVENTOR(S) : DIEGO FIGUERA

It is certified that error appears in the above-identified patent and that said Letters Patent is hereby corrected as shown below:

Column 3

Line 55, change "wall" to --well--.

Column 5

Line 32, between "Therefore" and "the", insert --,--.

Column 8, line 10
(Claim 17, line 3)

Change "implanation" to --implantation--.

Column 8, line 33
(Claim 9, line 1)

Change "caridac" to --cardiac--.

Signed and Sealed this

Fifteenth Day of May 1984

[SEAL]

Attest:

GERALD J. MOSSINGHOFF

Attesting Officer

Commissioner of Patents and Trademarks